(12) United States Patent
Clayton

(10) Patent No.: US 8,460,377 B2
(45) Date of Patent: Jun. 11, 2013

(54) METHOD OF RELIEVING TMJ DISCOMFORT USING AN EAR INSERT

(75) Inventor: Lawrence G. Clayton, Rockford, IL (US)

(73) Assignee: Ascentia Health, Inc., Rockford, IL (US)

( * ) Notice: Subject to any disclaimer, the term of this patent is extended or adjusted under 35 U.S.C. 154(b) by 42 days.

(21) Appl. No.: 13/215,188

(22) Filed: Aug. 22, 2011

(65) Prior Publication Data

US 2011/0307009 A1 Dec. 15, 2011

Related U.S. Application Data

(62) Division of application No. 12/075,046, filed on Mar. 7, 2008, now Pat. No. 8,002,829.

(51) Int. Cl.
*A61F 2/18* (2006.01)

(52) U.S. Cl.
USPC ............................................................. 623/10

(58) Field of Classification Search
USPC .................... 623/10; 381/328–329, 370–374, 381/380; 128/864
See application file for complete search history.

(56) References Cited

U.S. PATENT DOCUMENTS

| | | |
|---|---|---|
| 2,230,738 A | 2/1941 | Baum |
| 4,094,303 A | 6/1978 | Johnston |
| 4,776,322 A | 10/1988 | Hough et al. |
| 5,203,352 A | 4/1993 | Gardner, Jr. |
| 5,381,484 A | 1/1995 | Claes et al. |
| 5,395,168 A | 3/1995 | Leenen |
| 5,480,433 A | 1/1996 | Nadol, Jr. |
| 5,519,782 A * | 5/1996 | Shinohara et al. ............ 381/370 |
| 5,553,152 A | 9/1996 | Newton |
| 5,573,015 A | 11/1996 | Williams |
| 5,645,584 A | 7/1997 | Suyama |
| 5,717,771 A | 2/1998 | Sauer et al. |
| 5,769,891 A | 6/1998 | Clayton |
| 6,055,319 A | 4/2000 | Shennib et al. |
| 6,122,388 A | 9/2000 | Feldman |
| 6,337,915 B1 | 1/2002 | Lewis |
| 7,536,023 B2 | 5/2009 | Leedom et al. |
| 2006/0098833 A1 | 5/2006 | Juneau et al. |
| 2007/0183613 A1 | 8/2007 | Juneau et al. |
| 2009/0228103 A1 | 9/2009 | Clayton |

OTHER PUBLICATIONS

U.S. Patent & Trademark Office, International Search Report in International Patent Application No. PCT/US2008/077339 (Nov. 26, 2008).

(Continued)

*Primary Examiner* — David Isabella
*Assistant Examiner* — Marcia Hoffman
(74) *Attorney, Agent, or Firm* — Paul A. Jenny; Jinwon Jung; Michael Best & Friedrich, LLP

(57) ABSTRACT

A prosthesis for insertion in an ear to reduce pain resulting from TMJ disorders. The ear insert has a predefined shape conforming to the shape of the ear canal when the jaw is in an open position. The ear insert supports the TMJ and associated secondary musculature to reduce strain in the TMJ area, including the muscles, ligaments, nerves, and the temporomandibular joint itself. The insert is hollow in the inside to permit hearing and is made of a rigid material which retains the shape of the ear canal. A scalloped indenture extends across a surface of the ear insert positioned behind the tragus.

23 Claims, 1 Drawing Sheet

OTHER PUBLICATIONS

U.S. Patent & Trademark Office, Written Opinion in International Patent Application No. PCT/US2008/077339 (Nov. 26, 2008).
U.S. Patent & Trademark Office, International Search Report in International Patent Application No. PCT/US2010/048613 (Nov. 1, 2010).
U.S. Patent & Trademark Office, Written Opinion in International Patent Application No. PCT/US2010/048613 (Nov. 1, 2010).
U.S. Patent & Trademark Office, International Preliminary Report on Patentability in International Patent Application No. PCT/US2008/077339 (May 6, 2011).

* cited by examiner

METHOD OF RELIEVING TMJ DISCOMFORT USING AN EAR INSERT

CROSS-REFERENCE TO RELATED APPLICATIONS

This patent application is a divisional of copending U.S. patent application Ser. No. 12/075,046, filed Mar. 7, 2008, which is pending and is incorporated by reference in its entirety herein.

TECHNICAL FIELD

The present disclosure relates generally to medical devices, and more particularly, to medical devices for alleviation of jaw discomfort.

BACKGROUND

Many people suffer from pain in the joint located between the skull and the jaw. The joint is formed between the temporal bone of the skull and the mandible or jaw bone, and is commonly known as the temporo-mandibular joint or "TMJ". The human body has two temporo-mandibular joints, one located on each side of the jaw in front of each ear. The TMJs move every time a person chews, talks, or swallows.

In greater detail, the TMJ is a paired joint articulating the mandibular condyle, articulator disc, and squamous portion of the temporal bone. The TMJ is capable of both glide and hinge movements. Specifically, the TMJ is formed by the mandibular condyle fitting into the mandibular fossa of the temporal bone. A separation of these two bones is accomplished by the articulator disc which is composed of dense fibrous connective tissue. Ligaments attach the articulator disc to the condyle, permitting rotational movement of the articulator disc during mouth opening and closure.

Displacement of the articulator disc introduces strain to the jaw muscles and causes muscle pain or fatigue around the jaw. In addition, articulator disc displacement often causes a painful clicking in the TMJ during certain jaw movements as the disc moves between normal and displaced positions. A number of other symptoms may occur as a result of a strained disc, including TMJ lock, shoulder, neck, and back pain, and headaches.

Unfortunately, conventional methods of treating temporo-mandibular joint disorders can be costly, physically cumbersome, involve invasive and irreversible treatment or be time consuming. Some conservative methods for treating TMJ discomfort include the use of an intra-oral splint, medication, and life style changes. One type of intra-oral splint is a stabilization apparatus which is used to help alter the posture of the mandible to a more open, relaxed, resting position. Another type of intra-oral splint is an anterior positioning apparatus. The anterior positioning apparatus attempts to decrease the compression load on the joint and alter the structural condyle disc relation. Both types of splints, however, cannot be used full time without risking displacement of teeth. Treatment by medication often involves the use of addictive drugs and/or anti-depressants and therefore can lead to misuse and abuse. In addition, medications often produce adverse side effects in the patient. Other conservative methods include chiropractic or physical therapy. Unfortunately, these methods require extensive time commitments and physical exertion by the patient.

More aggressive treatment of TMJ discomfort includes orthodontic treatment such as grinding down of teeth and various types of surgery. Orthodontic treatments, however, merely indirectly address TMJ pain by adjusting the dental articulation and overall bite of the patient. Furthermore, orthodontic approaches are invasive, irreversible, and expensive.

An alternative procedure and related apparatus for treatment of TMJ discomfort are disclosed in U.S. Pat. No. 5,769,891, the contents of which are incorporated by reference herein in their entirety. According to the disclosure in U.S. Pat. No. 5,769,891, a prosthesis is provided for insertion into the ear canal. The prosthesis has a rigid structural portion of a shape conforming to the ear canal when the jaw is in an open position. The prosthesis provides added support to the TMJ and associated secondary musculature to reduce strain in the TMJ area.

SUMMARY OF THE DISCLOSURE

According to one aspect, the present disclosure provides an ear canal insert for treating TMJ disorders which acts directly on the TMJ and associated ligament and muscle structures to reduce stress and loads placed on the articulator disc located between the temporal bone and the mandible, as well as supportive muscles and ligaments near the TMJ. The insert includes a base portion adapted to reside adjacent the opening of the ear canal with a portion of the base support extending into the inter-tragal notch to reside at a position between the tragus and anti-tragus portions of the outer ear following insertion. The base portion further includes a scalloped indenture extending away from a boundary edge of the base portion across an outwardly facing lateral surface of the insert.

According to another aspect, the present disclosure provides an ear canal insert for treating TMJ disorders which acts directly on the TMJ and associated ligament and muscle structures to reduce stress and loads placed on the articulator disc located between the temporal bone and the mandible, as well as supportive muscles and ligaments near the TMJ. The insert includes a base portion adapted to reside adjacent the opening of the ear canal following insertion. At least one anterior projecting post element projects outwardly away from a boundary edge of the base portion to a position outside of the ear canal to facilitate insertion and removal of the insert.

These and other aspects of the disclosure will become more apparent from the following detailed description when taken in conjunction with the accompanying drawings.

Figure 1:
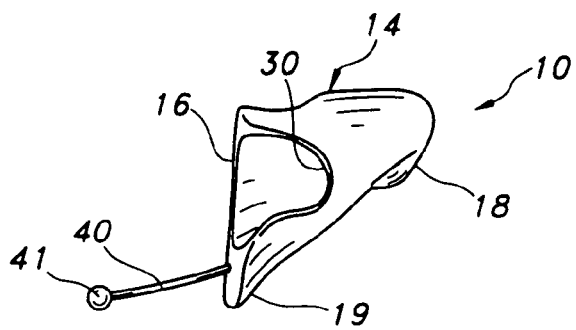
FIG. 1 is an isometric view of an exemplary prosthesis for insertion into an ear canal for treatment of TMJ discomfort.

While the concepts of the instant disclosure are susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions and equivalents falling within the spirit and scope of the disclosure as defined by the appended claims and all equivalents thereto.

DETAILED DESCRIPTION OF EXEMPLARY EMBODIMENTS

Exemplary constructions and practices will now be described through reference to the drawings, wherein like elements are designated by like reference numerals in the various views. For purposes of illustration, FIG. 1 illustrates a prosthesis 10 adapted for insertion into an ear canal 12 as shown generally in FIG. 3. According to a contemplated practice, the prosthesis 10 includes a hollow structural body portion 14 molded from a substantially rigid material such as acrylic or the like. Accordingly, the structural body portion 14 is substantially incompressible and maintains its shape upon insertion.

In the illustrated construction, the structural body portion 14 is substantially hollow along its length to facilitate sound transmission. The structural body portion 14 has a three-dimensional exterior shape corresponding substantially to the shape of ear canal 12 when a user's mouth is in an open position. Thus, following insertion of the prosthesis 10, the structural body portion 14 is in substantially conforming relation relative to contours at the inner surface of the ear canal 12 such that the prosthesis 10 is held in a substantially nested relation relative to the interior surface of the ear canal 12. If desired, one or more additional compressible cushioning layers (not shown) may be provided around at least apportion of the rigid structural body portion 14. However, such a cushioning layer is in no way essential. By way of example only, and not limitation, materials for forming such a cushioning layer may include PVC, silicone or the like.

Figure 2:
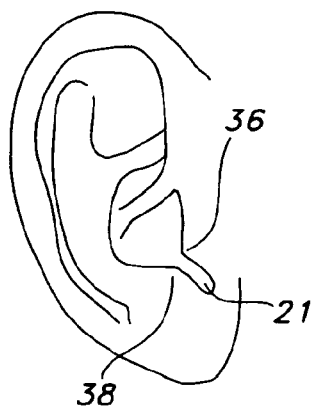
FIG. 2 is a view illustrating an outer ear.
Figure 3:
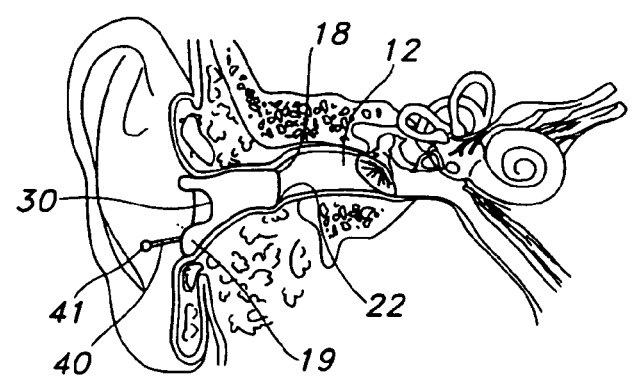
FIG. 3 is cut-away side view of the prosthesis of FIG. 1 inserted into an ear canal.

As shown in the illustrated construction, the structural body portion 14 includes a proximal base portion 16 and a distal end portion 18. The proximal base portion 16 is of greater diameter than the distal end portion 18. As best illustrated in FIG. 3, the proximal base portion 16 is adapted to be positioned in inserted relation substantially adjacent the opening of ear canal 12. In the illustrated construction, the proximal base portion 16 includes an extended peninsular leg portion 19 adapted to project generally downwardly when the structural body portion 14 is in inserted position within the ear canal 12. In this regard, the peninsular leg portion 19 projects into the inter-tragal notch 21 shown in FIG. 2 adjacent to the tragus 36 and the opposing anti-tragus 38 portions of the outer ear. The distal end portion 18 of the structural body portion 14 is adapted to extend approximately to the bend in the ear canal known as the isthmus 22. The isthmus 22 is in close proximity to the temporo-mandibular joint and is located approximately 20-22 millimeters from the outside of an adult ear. However, this distance may vary in different individuals.

As best illustrated through joint reference to FIGS. 1 and 3, according to the illustrated construction, a scalloped indenture 30 extends away from an edge of the proximal base portion 16. In this regard, it is contemplated that the scalloped indenture 30 may be formed by any suitable technique as may be desired. By way of example only, and not limitation, one such technique involves post-formation sculpting using cutting tools or the like although other techniques may be used as desired. As shown, the scalloped indenture 30 extends generally towards the distal end portion 18 and is positioned across a surface of the structural body portion 14 adapted reside immediately behind the tragus 36 and opposing anti-tragus 38 of the outer ear. It is contemplated that the scalloped indenture 30 may have a length and width suitable to accept substantially the entire lobe of the tragus 36 thereby facilitating the ability of the tragus 36 to bend inwardly towards the opening of ear canal 12 substantially without obstruction. Surprisingly, it has been found that the structural body portion 14 incorporating such a scalloped indenture 30 maintains its structural integrity to provide jaw support as described further hereinafter despite the substantial reduction in supporting material.

According to the illustrated construction, it is contemplated that at least one anterior projecting post element 40 may extend away from a surface of the peninsular leg portion 19. As shown, the post element 40 projects in a direction extending generally away from the distal end portion 18 so as to project towards the exterior of the ear. Following insertion, at least a portion of the post element 40 may reside outside of the ear canal 12 at a position within the vicinity of the inter-tragal notch 21. In this position, a wearer may grasp the post element 40 to facilitate removal of the insert.

The post element 40 is preferably substantially pliable to enhance insertabilty and removability and to avoid discomfort to the wearer. At the same time, the post element 40 should be characterized by sufficient strength to avoid breakage. By way of example only, and not limitation, it has been found that a suitable post element 40 may be formed from thermoplastic monofilament nylon adhesively bonded onto a surface of the peninsular leg portion 19. However, other suitable polymeric or non-polymeric materials may likewise be utilized if desired.

As shown, the post element 40 may include a bulbous head portion 41. Such a bulbous head portion 41 may enhance the ability of a wearer to grasp the post element 40 during removal of the prosthesis 10 from the ear canal 12. In the event that the post element 40 is formed from nylon or other thermoplastic material, a suitable bulbous head portion 41 may be formed by selectively melting the terminal end of the post element 40 to form a melted polymer bead which is thereafter permitted to resolidify. The surface of the resolidified bead may thereafter be smoothed by sanding or other suitable treatment to remove irregularities so as to enhance comfort during use.

Figure 4:
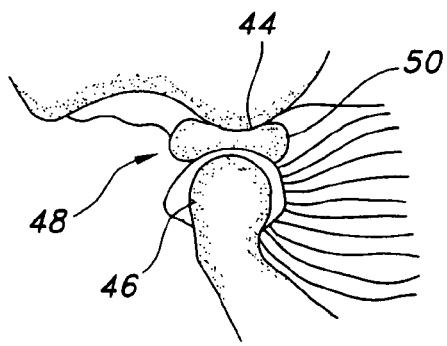
FIG. 4 is a side view of a TMJ in an unoccluded position showing a disc in the normal position.
Figure 5:
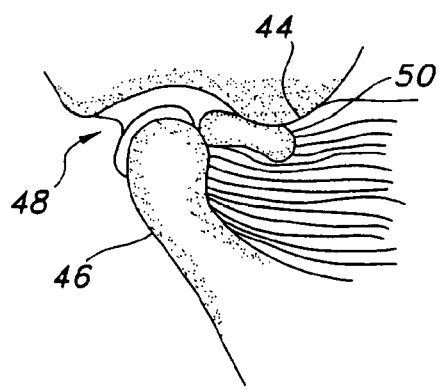
FIG. 5 is a side view of a TMJ in the closed position showing a disc in the displaced position.

Referring now to FIGS. 4 and 5, the use of the prosthesis 10 influences the relationship between the temporal bone 44 and the mandible 46 in each temporo-mandibular joint 48, thereby relieving pain inducing stress in the temporo-mandibular joint 48 and related muscles, ligaments, and nerves. In this regard, it will be appreciated that one source of temporo-mandibular joint discomfort is a dislocated articulator disc 50. As shown in FIG. 4, when the jaw or mandible 46 is in an open or unoccluded position corresponding to the mouth being open, the articulator disc 50 is usually in a normal, unstrained position between the temporal bone 44 and a condyle surface of the mandible 46. As is often the case with a person experiencing temporo-mandibular joint discomfort, the articulator disc 50 slips to a displaced position when the mandible 46 is subsequently closed, as illustrated in FIG. 5. The displacement of the articulator disc 50 is often indicated by a clicking or popping noise as the mandible 46 moves between open and closed positions. In the displaced position, the articulator disc 50 is no longer between the condyle surface and the temporal bone 44, and the articulator disc 50 and attached ligaments become strained. Strain on these members stresses the surrounding muscles, which may ultimately result in face, neck, and back pain.

To treat temporo-mandibular joint discomfort arising from a displaced articulator disc 50, the prosthesis 10 is provided for reducing stresses and loads on the articulator disc 50. The prosthesis 10 reshapes the ear canal and provides a rigid structure which helps align the temporo-mandibular joint 48 and associated muscle and ligament structures so that the temporo-mandibular joint 48 has a normal rotational movement. Strain or compression on the articulator disc 50 is therefore reduced, thereby alleviating pain in the temporo-mandibular joint and associated structures.

It is to be understood a dislocated disc is only one cause of temporo-mandibular joint discomfort and that there are many other sources of such pain. Nerves, ligaments, and muscle groups (such as the masticatory musculature) are located proximal to the temporo-mandibular joint, and improper loading, strain, or alignment of these members provide potential sources of temporo-mandibular joint pain. Rather than being limited to disc dislocation situations, as outlined above, the prosthesis 10 addresses misalignment and stress in the temporo-mandibular joint and related structures by supporting these structures for normal rotational movement.

It will be appreciated that the prosthesis 10 alleviates temporo-mandibular joint discomfort by supporting the temporo-mandibular joint 48 and associated muscles, nerves, and ligaments for proper rotation of the mandible between open and closed positions. The prosthesis 10 is formed to correspond to the shape of the ear canal 12 when the mandible 46 is open and disc 50 is in the normal position. When the mandible 46 is subsequently closed, the prosthesis 10 maintains the positioning of the mandible 46 the so that the disc 50 is not displaced. Accordingly, a natural body orifice is used to reposition the mandible 46 without requiring surgery or other painful and invasive techniques. As noted above, the example of a dislocated disc is merely illustrative of a temporo-mandibular joint condition addressed by the present device and is in no means meant to limit the scope of the present invention. Accordingly, it will be appreciated that the present device addresses stresses and misalignments in not only the disc but also any muscles, ligaments, and nerves associated with the temporo-mandibular joint.

It will be appreciated that the foregoing description provides examples of the disclosed apparatus and method of use. However, it is contemplated that other implementations of the disclosure may differ in detail from the foregoing examples. All references to examples herein are intended to reference the particular example being discussed at that point and are not intended to imply any limitation as to the scope of the disclosure or claims more generally. All language of distinction and disparagement with respect to certain features is intended to indicate a lack of preference for those features, but not to exclude such from the scope of the claims entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure contemplates the inclusion of all modifications and equivalents of the subject matter recited in the appended claims as permitted by applicable law. Moreover, any combination of the above-described elements in all possible variations thereof is contemplated unless otherwise indicated herein or otherwise clearly contradicted by context.

What is claimed is:

1. A method of treating discomfort in a joint between a mandible and a corresponding temporal bone, the method comprising:
   inserting a prosthesis into an ear canal in an ear having a tragus, wherein the ear canal includes an isthmus, wherein the prosthesis comprises a substantially rigid structural body having a predefined shape substantially conforming to a contour of a portion of the ear canal which extends approximately between an entrance to the ear canal and the isthmus when a jaw is in an open position, the structural body having a rigidity such that it does not compressibly deform upon insertion into the ear canal or when the jaw is in a closed position, the structural body being hollow along its length to facilitate sound transmission, the structural body including a proximal base portion positioned adjacent to the entrance of the ear canal, the structural body further including a distal end portion adapted to extend an effective distance into the ear canal, the structural body further including a scalloped indenture extending away from a boundary edge of the proximal base portion, wherein the scalloped indenture is an opening into the hollow structural body, the scalloped indenture including a length dimension extending in a longitudinal direction of the structural body from the proximal base towards the distal end portion with a wall of the structural body disposed at least partially about a perimeter of the scalloped indenture, the scalloped indenture being positioned behind the tragus of the ear.

2. The method as recited in claim 1, wherein the structural body is free from any covering.

3. The method as recited in claim 1, wherein said structural body is formed from acrylic.

4. The method as recited in claim 1, wherein said scalloped indenture is sized for an identified user and is characterized by the length and a width sufficient to receive and at least partially surround the tragus of the ear of the identified user.

5. The method as recited in claim 1, wherein at least one post element projects away from the proximal base portion, the post element extending to a position outside of the ear canal when the prosthesis is inserted within the ear canal.

6. The method as recited in claim 5, wherein said post element is formed from a thermoplastic polymeric material.

7. The method as recited in claim 6, wherein said post element is formed from monofilament nylon.

8. The method as recited in claim 1, wherein the proximal base portion includes an extended peninsular leg portion adapted to extend to an inter-tragal notch.

9. The method as recited in claim 8, wherein at least one post element projects away from the extended leg portion, the post element extending to a position outside of the ear canal when the prosthesis is inserted within the ear canal.

10. The method as recited in claim 1, wherein the scalloped indenture is a cutout in the wall of the structural body beginning at the boundary edge and extending in the longitudinal direction away from the boundary edge of the proximal base portion.

11. A method of treating discomfort in a joint between a mandible and a corresponding temporal bone, the method comprising:
   moving the mandible to an open position;
   providing a prosthesis having a structural body, the structural body being hollow along its length to facilitate sound transmission, the structural body having a proximal base portion and a distal end portion, the structural body further including a scalloped indenture having a length dimension extending in a longitudinal direction of the structural body from the proximal base towards the distal end portion, wherein the scalloped indenture is an opening into the hollow structural body; and
   inserting the prosthesis into an ear canal in an ear having a tragus such that the scalloped indenture is disposed directly behind the tragus.

12. The method as recited in claim 11, where the structural body is substantially rigid and has a predefined shape substantially conforming to a contour of a portion of the ear canal which extends approximately between an entrance to the ear canal and an isthmus of the ear canal when the mandible is in the open position.

13. The method as recited in claim 11, wherein the structural body is free from any covering.

14. The method as recited in claim 11, wherein the structural body is formed from acrylic.

15. The method as recited in claim 11, wherein the scalloped indenture is sized for an identified user and is characterized by the length and a width sufficient to receive and at least partially surround the tragus of the ear of the identified user.

16. The method as recited in claim 11, wherein the proximal base portion is positioned adjacent to an entrance of the ear canal.

17. The method as recited in claim 16, wherein at least one post element projects away from the proximal base portion, the post element extending to a position outside of the ear canal when the prosthesis is inserted within the ear canal.

18. The method as recited in claim 17, wherein said post element is formed from a thermoplastic polymeric material.

19. The method as recited in claim 18, wherein said post element is formed from monofilament nylon.

20. The method as recited in claim 16, wherein the proximal base portion includes an extended peninsular leg portion adapted to extend to an inter-tragal notch.

21. The method as recited in claim 20, wherein at least one post element projects away from the extended leg portion, the post element extending to a position outside of the ear canal when the prosthesis is inserted within the ear canal.

22. The method as recited in claim 11, wherein the scalloped indenture is a cutout in a wall of the structural body beginning at a boundary edge of the proximal base portion and extending in the longitudinal direction away from the boundary edge of the proximal base portion.

23. The method as recited in claim 11, wherein the distal end portion is adapted to extend an effective distance into the ear canal to reduce strain on the joint.

\* \* \* \* \*